(12) United States Patent
George et al.

(10) Patent No.: US 10,744,073 B2
(45) Date of Patent: Aug. 18, 2020

(54) MOLDABLE SOLID CLEANSING COMPOSITIONS

(71) Applicant: L'Oreal, Paris (FR)

(72) Inventors: Kelly Marie George, Denville, NJ (US); Allison Elder, North Adams, MA (US); Miao Wang, Westfield, NJ (US); Carol Elmasry, South Amboy, NJ (US); Kaitlin M. Traister, Conshohocken, PA (US)

(73) Assignee: L'Oreal, Paris (FR)

( * ) Notice: Subject to any disclaimer, the term of this patent is extended or adjusted under 35 U.S.C. 154(b) by 699 days.

(21) Appl. No.: 15/058,073

(22) Filed: Mar. 1, 2016

(65) Prior Publication Data

US 2017/0252272 A1 Sep. 7, 2017

(51) Int. Cl.
| | | |
|---|---|---|
| *A61K 8/00* | (2006.01) | |
| *A61K 8/02* | (2006.01) | |
| *A61K 8/37* | (2006.01) | |
| *A61Q 19/10* | (2006.01) | |
| *A61K 8/92* | (2006.01) | |
| *A61Q 1/14* | (2006.01) | |

(52) U.S. Cl.
CPC ............ *A61K 8/0216* (2013.01); *A61K 8/37* (2013.01); *A61K 8/922* (2013.01); *A61Q 1/14* (2013.01); *A61Q 19/10* (2013.01); *A61K 2800/31* (2013.01)

(58) Field of Classification Search
None
See application file for complete search history.

(56) References Cited

U.S. PATENT DOCUMENTS

| | | | | |
|---|---|---|---|---|
| 2006/0002875 | A1* | 1/2006 | Winkler | A61K 8/11 424/63 |
| 2007/0196400 | A1* | 8/2007 | Raschke | A61K 8/06 424/401 |
| 2009/0304617 | A1* | 12/2009 | Banowski | A61K 8/02 424/68 |
| 2012/0028916 | A1* | 2/2012 | Fournial | A61K 8/347 514/33 |

FOREIGN PATENT DOCUMENTS

| | | |
|---|---|---|
| KR | 101347727 B1 | 1/2014 |
| WO | 2012095410 A1 | 7/2012 |
| WO | 2014098253 A1 | 6/2014 |
| WO | 2014098254 A1 | 6/2014 |

* cited by examiner

*Primary Examiner* — Necholus Ogden, Jr.
(74) *Attorney, Agent, or Firm* — Christensen O'Connor Johnson Kindness PLLC (57) ABSTRACT

Described herein are anhydrous compositions including at least one oil phase and at least one non-ionic surfactant. The oil phase includes one or more linear (i.e., unbranched) fatty esters, such as cetyl palmitate. The oil phase can further include at least one branched fatty esters, such as ethylhexyl palmitate and/or isocetyl stearate.

16 Claims, 8 Drawing Sheets

FIG. 1

COMPARATIVE EXAMPLES

| Ingredient | Ex #1 (comparative) | Ex #2 (comparative) | Ex #3 (comparative) | Ex #4 (comparative) | Ex #5 (comparative) | Ex #6 (comparative) | Ex #7 (comparative) |
|---|---|---|---|---|---|---|---|
| ISOCETYL STEARATE | | | | | | 4.9 | 1.9 |
| ETHYLHEXYL PALMITATE | 82.4 | 82.4 | 82.4 | 82.4 | 82.4 | 45.00 | 45.00 |
| SILICA SILYLATE | | | | | | 0.5 | 0.5 |
| CETYL PALMITATE | | | | | | 25 | 25 |
| SYNTHETIC WAX | | 9 | | | | | |
| POLYETHYLENE | 9 | | 9 | 9 | 9 | 8 | 8 |
| OLEA EUROPAEA (OLIVE) FRUIT OIL | 1 | 1 | 1 | 1 | 1 | 1 | 1 |
| BUTYROSPERMUM PARKII (SHEA) BUTTER | 1 | 1 | 1 | 1 | 1 | 1 | 1 |
| STEARYL ALCOHOL | | | | | | 3 | 6 |
| CAPRYLYL GLYCOL | 0.5 | 0.5 | 0.5 | 0.5 | 0.5 | 0.5 | 0.5 |
| PEG-20 GLYCERYL TRIISOSTEARATE | 5 | 5 | | | | 5 | 5 |
| PEG-8 STEARATE | | | 5 | | | | |
| PEG-7 GLYCERYL COCOATE | | | | 5 | | | |
| PEG-7 CAPRYLIC/CAPRIC GLYCERIDES | | | | | 5 | | |
| NEOPENTYL GLYCOL DIHEPTANOATE | | | | | | 5 | |
| VACCINIUM MYRTILLUS FRUIT EXTRACT (and) SACCHARUM OFFICINARUM (SUGAR CANE) EXTRACT (and) CITRUS AURANTIUM DULCIS (ORANGE) FRUIT WATER (and) CITRUS LIMON (LEMON) FRUIT EXTRACT (and) ACER SACCHARUM (SUGAR MAPLE) EXTRACT | 0.1 | 0.1 | 0.1 | 0.1 | 0.1 | 0.1 | 0.1 |
| TOCOPHEROL (and) TOCOPHEROL (and) TOCOPHEROL (and) TOCOPHEROL | 0.5 | 0.5 | 0.5 | 0.5 | 0.5 | 0.5 | 0.5 |
| FRAGRANCE | 0.5 | 0.5 | 0.5 | 0.5 | 0.5 | 0.5 | 0.50 |
| TOTAL % | 100.00 | 100.00 | 100.00 | 100.00 | 100.00 | 100.00 | 100.00 |
| INITIAL ASPECT: | White balm | White balm | White balm | White balm | White balm | White balm | White balm |
| Moldability (popping from mold/cup after hot pouring then cooling): Pass or Fail | Fail: too soft, did not retain shape | Fail: too soft, did not retain shape | Fail: very soft, could not pop out of molds | Fail: very soft, could not pop out of molds | Fail: very soft, could not pop out of molds | Pass: retains shape & pops out of molds | Pass: retains shape & pops out of molds |
| HARDNESS (gforce, via Texture Analyzer) | 20.30 | NA | NA | NA | NA | 135.12 | 144.70 |
| Texture Transformation (easily spreads into a creamy oil with little to no crumbling) & Skin Feel: 1-3 rating, 1=good, 2=moderate, 3=poor | Rating =2. A bit too soft to handle but spreads easily | Rating=2. A bit too soft to handle but spreads easily | Rating=2. Too soft to handle, messy application | Rating=2. Too soft to handle, messy application | Rating=2. Too soft to handle, messy application | Rating=2. Modest texture transformation, somewhat too hard/draggy | Rating=2. Modest texture transformation, somewhat too hard/draggy |
| STABILITY RESULTS: | NA | NA | NA | NA | NA | FAILED - see separation/crystallization | FAILED - see separation/crystallization |

FIG. 2

INVENTIVE EXAMPLES

| Ingredient | Ex. #8 (Inventive) | Ex. #9 (Inventive) | Ex. #10 (Inventive) | Ex. #11 (Inventive) | Ex. #12 (Inventive) | Ex. #13 (Inventive) | Ex. #14 (Inventive) | Ex. #15 (Inventive) |
|---|---|---|---|---|---|---|---|---|
| ISOCETYL STEARATE | 34.4 | 29.4 | 19.4 | 17.4 | 7.4 | 6.9 | 6.9 | 6.9 |
| ETHYLHEXYL PALMITATE | 25 | 25 | 35 | 35 | 45 | 65 | 65 | 35 |
| SILICA SILYLATE | | | | | | 0.5 | 0.5 | 0.5 |
| CETYL PALMITATE | 25 | 25 | 25 | 25 | 25 | 25 | 15 | 20 |
| POLYETHYLENE | 7 | 7 | 7 | 8 | 8 | 8 | 8 | 6 |
| OLEA EUROPAEA (OLIVE) FRUIT OIL | 1 | 1 | 1 | 1 | 1 | 1 | 1 | 1 |
| BUTYROSPERMUM PARKII (SHEA) BUTTER | | | | | | | | 1 |
| BUTYROSPERMUM PARKII (SHEA) BUTTER | 1 | | | | | | | 1 |
| CETYL ALCOHOL | | | | | | | | 2 |
| CAPRYLYL GLYCOL | 0.5 | 0.5 | 0.5 | 0.5 | 0.5 | 0.5 | 0.5 | 0.5 |
| PEG-30 GLYCERYL TRIISOSTEARATE | 5 | 5 | 5 | 5 | 5 | 5 | 5 | 5 |
| NEOPENTYL GLYCOL DIHEPTANOATE | | | | | | | | |
| VACCINIUM MYRTILLUS FRUIT EXTRACT (and) SACCHARUM OFFICINARUM (SUGAR CANE) EXTRACT (and) CITRUS AURANTIUM DULCIS (ORANGE) FRUIT WATER (and) CITRUS LIMON (LEMON) FRUIT EXTRACT (and) ACER SACCHARUM (SUGAR MAPLE) EXTRACT | 0.1 | 0.1 | 0.1 | 0.1 | 0.1 | 0.1 | 0.1 | 0.1 |
| TOCOPHEROL (and) TOCOPHEROL (and) TOCOPHEROL (and) TOCOPHEROL | 0.5 | 0.5 | 0.5 | 0.5 | 0.5 | 0.5 | 0.5 | 0.5 |
| FRAGRANCE | 0.5 | 0.5 | 0.5 | 0.5 | 0.5 | 0.5 | 0.5 | 0.5 |
| TOTAL % | 100.000 | 100.000 | 100.000 | 100.000 | 100.000 | 100.000 | 100.000 | 100 |
| INITIAL ASPECT | Solid, white balm | Solid, white balm | Solid, white balm | Solid, white balm | Solid, white balm | Solid, white balm | Solid, white balm | Solid, white balm |
| Moldability (popping from mold/cap after hot pouring then cooling): Pass or Fail | Pass: retains shape & pops out of molds | Pass: retains shape & pops out of molds | Pass: retains shape & pops out of molds | Pass: retains shape & pops out of molds | Pass: retains shape & pops out of molds | Pass: retains shape & pops out of molds | Pass: retains shape & pops out of molds | Pass: retains shape & pops out of molds |
| Hardness (g-force, using Texture Analyzer) | 114.36 | 108.00 | 105.50 | 97.30 | 128.00 | 101.51 | 72.56 | 80.71 |
| Texture Transformation: freely spreads into a creamy oil which lets to the crumble) & Skin Feel: 1-3 rating, 1=good, 2=moderate, 3=poor | Rating=1, Good spreadability and texture transformation | Rating=1, Good spreadability and texture transformation | Rating=1, Good spreadability and texture transformation | Rating=1, Good spreadability and texture transformation | Rating=1, Good spreadability and texture transformation | Rating=1, Good spreadability and texture transformation, nice skin feel during application and rinse-off | Rating=1, Good spreadability and texture transformation, nice skin feel during application and rinse-off | Rating=1, Good spreadability and texture transformation, nice skin feel during application and rinse-off |
| STABILITY RESULTS | Passed 8 weeks stability at all temperature conditions (5C, 25C, 37C & 45C) | Passed 8 weeks stability at all temperature conditions (5C, 25C, 37C & 45C) | Passed 8 weeks stability at all temperature conditions (5C, 25C, 37C & 45C) | Passed 8 weeks stability at all temperature conditions (5C, 25C, 37C & 45C) | Passed 8 weeks stability at all temperature conditions (5C, 25C, 37C & 45C) | Passed 8 weeks stability at all temperature conditions (5C, 25C, 37C & 45C) | Passed 8 weeks stability at all temperature conditions (5C, 25C, 37C & 45C) | Passed 8 weeks stability at all temperature conditions (5C, 25C, 37C & 45C) |

*FIG. 3*

Prior Art Example

| Ingredient | Ex #1 (External comparative) |
|---|---|
| MINERAL OIL | 51.00 |
| CETYL ETHYLHEXANOATE | 30 |
| SILICA SILYLATE* | 0.50 |
| POLYETHYLENE | 6.5 |
| PEG-20 GLYCERYL TRIISOSTEARATE | 10 |
| WATER | 0.50 |
| BUTYLENE GLYCOL | 0.50 |
| TOCOPHEROL (and) TOCOPHEROL (and) TOCOPHEROL (and) TOCOPHEROL | 0.5 |
| FRAGRANCE | 0.5 |
| TOTAL %: | 100.00 |
| INITIAL ASPECT: | Off-white/slight yellow balm |
| Moldability (popping from mold/cup after hot pouring then cooling): Pass or Fail | FAIL: too soft, did not retain shape |
| HARDNESS (g/force, via Texture Analyzer) | 27.45 |
| Texture Transformation (easily spreads into a creamy oil with little to no crumbling) & Skin Feel: 1-3 rating. 1=good, 2=moderate, 3=poor | Rating=3: Too soft. Spreads easily but rinseability is poor. |

* 0.5% was used because 5% would equal >100
Percentages were modified slightly so that the sum equals 100 %

MOLDABLE SOLID CLEANSING COMPOSITIONS

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present disclosure features an anhydrous composition including an oil phase and at least one non-ionic surfactant. The oil phase includes at least one linear fatty ester. The composition is solid at ambient temperature (25° C.) with a hardness of at least 35 g-force, retains a molded shape when subjected to a pop-out test at ambient temperature; and undergoes a solid to cream transition over a period spanning from an initial application up to 1 to 5 minutes (e.g., up to 5 minutes, up to 4 minutes, up to 3 minutes, up to 2 minutes, or up to 1 minute) at ambient temperature, when applied manually or using an electronic device to a skin portion.

In another aspect, the present disclosure features a method of cleansing using the compositions of the present disclosure at ambient temperature.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 2 is a table providing compositional and testing information regarding comparative compositions;

FIG. 3 is a table providing compositional and testing information regarding exemplary compositions in accordance with embodiments disclosed herein;

DETAILED DESCRIPTION

For users of facial makeup, there is an ongoing requirement of effective removal of existing makeup before application of new makeup, such that good skin health can be maintained and application of new makeup can be facilitated.

While facial makeup includes a variety of formulations, which may have varying difficulty in removal, typical methods of makeup removal include pre-moistened towelettes, wipes, or pads; or a liquid makeup removal product (e.g., a single or biphase liquid or cream-in-tube), applied with cotton pads or balls or manually; or anhydrous, oil-based cleansing balm (e.g., a "balm-in-pot"). Many users of the balm-in-pot removal products are dissatisfied with the difficulty of extracting the balm from its container and applying the balm to a skin portion that has a makeup. Specifically, the balm tends to soil fingers in a manner that requires a separate cleansing step (e.g., hand washing) that detracts from the user's experience. Nonetheless, balm-style makeup removers are very effective once applied. Therefore, a makeup removal product that provides the cleansing effects of a balm but with an improved application experience for the user would be desirable.

Accordingly, disclosed herein are user friendly, aesthetically pleasing compositions suitable for makeup removal. The compositions are moldable at room temperature, therefore providing a solid form, in contrast to makeup removal compositions that are provided as liquids or gels in tubes or tubs. The compositions are configured such that rubbing or movement across the skin will transition the compositions from molded solid into a cream or lotion for makeup removal. A moldable composition brings additional benefits to the consumer as it can be provided in a pre-measured, single use quantity, to minimize waste and/or confusion of the amount of product needed. This smaller, moldable single-use format is also travel-friendly compared to typical size bottles, jars/pots.

Compositions

The compositions of the present disclosure are generally anhydrous compositions, such that they contain little to no water (e.g., less than 1% by weight water, relative to the total weight of the compositions). The compositions include at least one oil phase and at least one non-ionic surfactant. The oil phase includes one or more linear (i.e., unbranched) fatty esters, such as cetyl palmitate, which can assist in providing a molded shape to the compositions and/or provide skin benefits. In some embodiments, the oil phase can further include at least one branched fatty esters, such as ethylhexyl palmitate and/or isocetyl stearate, which can assist in providing skin cleansing properties, good skin feel, and skin care benefits.

In some embodiments, the compositions of the present disclosure include 70% to 95% (e.g., 70%-85%, 70% to 80%, 75% to 90%, 80% to 90%, 80% to 95%, or 90 to 95%) by weight of the oil phase, of which 1% to 30% by weight (e.g., 10% to 25% by weight) is the at least one linear (i.e., unbranched) fatty ester; and 4% to 8% (e.g., 4% to 6%, 5% to 8%, 6% to 8%) by weight of the at least one non-ionic surfactant, where the weight percentages are relative to the total weight of the compositions.

In some embodiments, the at least one linear fatty ester is present in a given composition in an amount of 1% to 30% by weight (e.g., 10% to 25% by weight), relative to the total weight of the composition. For example, the at least one linear fatty ester can be present in an amount of 1% or more (e.g., 5% or more, 10% or more, 20% or more, or 25% or more) and/or 30% or less (e.g., 25% or less, 20% or less, 10% or less, or 5% or less) by weight in the composition, relative to the total weight of the composition.

In some embodiments, the at least one linear fatty acid is cetyl palmitate.

In some embodiments, the at least one branched fatty ester is present in a given composition in an amount of 1% to 60% (e.g., 20% to 60%, 25% to 55%, 1 to 40%, or 5 to 35%) by weight, relative to the total weight of the composition. For example, the at least one branched fatty ester is present in a given composition in an amount of 1% or more (e.g., 5% or more, 20% or more, 25% or more, 35% or more, or 45% or more) and/or 60% or less (e.g., 45% or less, 35% or less, 25% or less, 20% or less, or 5% or less) by weight, relative to the total weight of the composition.

In some embodiments, the at least one branched fatty ester is ethylhexyl palmitate and/or isocetyl stearate.

In some embodiments, the compositions do not contain paraffin wax, mineral oil, or an anionic surfactant, or any combination thereof.

Oil Phase

As described above, the compositions of the present disclosure include an oil phase. The oil phase can include three major groups of compounds: oils (which include fats and butters), esters, and waxes. In some embodiments, in addition to the at least one linear fatty ester in the oil phase of the compositions, the oil phase further includes an oil, a wax, an ester, or any combination thereof. In some embodiments, in addition to the at least one linear fatty ester in the oil phase of the compositions, the oil phase further includes an oil, a wax, an ester, or any combination thereof; the ester can be other than a linear fatty ester. In certain embodiments, in addition to the at least one linear fatty ester in the oil phase of the compositions, the oil phase further includes an oil, a wax, an ester, or any combination thereof; the ester can be other than a linear or branched fatty ester. The oil phase can provide emollient properties to the compositions.

Oils

In some embodiments, when the oil phase further includes an oil, the oil is present in an amount of 0.5% to 20% (e.g., 1% to 20%, 1% to 15%, 5% to 15%, 5% to 10%, 0.5% to 5%, or 0.5% to 2%) by weight, relative to the total weight of the composition. For example, the oil can be present in a given composition in an amount of 0.5% or more (e.g., 1% or more, 2% or more, 5% or more, 10% or more, or 15% or more) and/or 20% or less (e.g., 15% or less, 10% or less, 5% or less, 2% or less, or 1% or less) by weight, relative to the total weight of the composition.

In some embodiments, when the oil phase further includes an oil, the oil can include natural oils. As used herein, the oil includes both oils and fats (which are generally solid at room temperature). Oils (including fats and butters) are glycerol esters composed of glycerol and fatty acids and are called triglycerides. The fatty acids can be saturated (no double bonds between the carbon atoms) or unsaturated (one or more double bonds), which can influence the stability and property of the oil. Oils having a high degree of saturated fatty acids (e.g., lauric, myristic, palmitic and stearic acids) include coconut oil, cottonseed oil, and palm oil. Oils with a high degree of unsaturated fatty acids (e.g., oleic, arachidonic, linoleic acid) include canola oil, olive oil, corn oil, almond oil, safflower oil, castor oil and avocado oil.

It is believed that saturated oils can be more stable and do not become rancid as quickly as unsaturated oils; while unsaturated oils can be smoother, more precious, less greasy, and better absorbed by the skin.

The oils in the oil phase can include natural butters such as shea butter, avocado butter, and/or cocoa butter. Natural butters can be good emollients and thickeners and, can have antioxidant and soothing properties (e.g., shea and avocado butters, which include phenolic compounds).

The oils can be of plant or animal origin. Examples of plant oils include linseed oil, camellia oil, macadamia nut oil, sunflower oil, apricot oil, soybean oil, arara oil, hazelnut oil, corn oil, olive oil, avocado oil, sasanqua oil, castor oil, safflower oil, jojoba oil, sunflower oil, almond oil, grapeseed oil, sesame oil, soybean oil, peanut oil, and mixtures thereof. Examples of animal oils include perhydrosqualene and squalane. In some embodiments, the oils can be botanical oils.

In some embodiments, the oil is olive oil, shea butter, linseed oil, camellia oil, macadamia nut oil, sunflower oil, apricot oil, soybean oil, arara oil, hazelnut oil, corn oil, avocado oil, sasanqua oil, castor oil, safflower oil, jojoba oil, sunflower oil, almond oil, grapeseed oil, sesame oil, soybean oil, peanut oil, avocado butter, cocoa butter, squalene, perhydrosqualene, or any combination thereof.

Waxes

In some embodiments, when the oil phase further includes a wax, the wax is present in an amount of 1% to 15% (e.g., 1 to 10%, 5 to 15%, 5% to 10%, 10% to 15%, or 5 to 8%) by weight, relative to the total weight of the composition. For example, the wax can be present in a given composition in an amount of 1% or more (e.g., 5% or more, 8% or more, 10% or more, or 12% or more) and/or 15% or less (e.g., 12% or less, 10% or less, 8% or less, or 5% or less) by weight, relative to the total weight of the composition.

In some embodiments, when the oil phase further includes a wax, the wax includes natural waxes and synthetic waxes (which include emulsifying waxes). In some embodiments, waxes include esters of a fatty acid and a fatty alcohol, and can be complex mixtures of heavy hydrocarbons and fatty acids combined with esters. As used herein, waxes do not include glycerides. In general, waxes can be harder, less greasy and more brittle than fats, and are resistant to moisture, oxidization and microbial attack. Waxes can be characterized by a high melting point (50-100° C.). In some embodiments, waxes (e.g., beeswax) can be an emollient and thickener, and can provide emulsifying properties. In certain embodiments, waxes (e.g., carnauba and candelilla wax) can provide hardness and have relatively high melting points. Synthetic waxes can include hydroxyoctacosanyl hydroxystearate, cetyl palmitate (or cetyl ester wax).

Waxes can include animal waxes (e.g., beeswax, lanolin), plant waxes (e.g., carnauba wax, candililla wax, jojoba wax), mineral waxes (e.g., ozokerite, microcrystalline wax including mixed refined hydrocarbons, ceresin, petrolatum), and synthetic waxes.

In some embodiments, the wax is selected from synthetic wax, carnauba wax, microcrystalline waxes, ozokerites, hydrogenated jojoba oil, polyethylene waxes (e.g., "Performalene 400 Polyethylene" and "Performalene 500 Polyethylene," available from New Phase Technologies), silicone waxes (e.g., poly($C_{24}$-$C_{28}$)alkylmethyldimethylsiloxane, available as "Abil Wax 9810" sold by the company Goldschmidt), $C_{20}$-$C_{40}$ alkyl stearate (e.g., "Kester Wax K82H" available from the company Kester Keunen), stearyl benzoate, shellac wax, and mixtures thereof. For example, the oil phase can include a wax selected from carnauba wax, candelilla wax, ozokerites, hydrogenated jojoba oil and polyethylene waxes. In some embodiments, the wax is candelilla wax, ozokerite, or mixtures thereof. In some embodiments, the wax is a polyethylene wax, a synthetic wax, a carnauba wax, a microcrystalline wax, an ozokerite, a hydrogenated jojoba oil, or a combination thereof.

Esters

As discussed above, the compositions of the present disclosure can include linear fatty esters, or a combination of linear and branched fatty esters. In some embodiments, the at least one linear fatty ester is present in a given composition in an amount of 1% to 30% by weight (e.g., 10% to 25% by weight), relative to the total weight of the composition. For example, the at least one linear fatty ester can be present in an amount of 1% or more (e.g., 5% or more, 10% or more, 20% or more, or 25% or more) and/or 30% or less (e.g., 25% or less, 20% or less, 10% or less, or 5% or less) by weight in the composition, relative to the total weight of the composition.

In some embodiments, the at least one branched fatty ester is present in a given composition in an amount of 1% to 60% (e.g., 20% to 60%, 25% to 55%, 1 to 40%, or 5 to 35%) by weight, relative to the total weight of the composition. For example, the at least one branched fatty ester is present in a given composition in an amount of 1% or more (e.g., 5% or more, 20% or more, 25% or more, 35% or more, or 45% or more) and/or 60% or less (e.g., 45% or less, 35% or less, 25% or less, 20% or less, or 5% or less) by weight, relative to the total weight of the composition. As used herein, a "branched fatty ester" includes fatty esters having cyclic moieties (e.g., sugars) and/or branched ester (e.g., branched hydrocarbons).

In some embodiments, fatty esters are obtained by direct reaction of fatty acids with alcohols. Examples of the fatty esters of fatty alcohols and/or of fatty acids include fatty esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the fatty esters being greater than or equal to 10.

In some embodiments, the fatty esters can be monoesters, such as dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; cetyl palmitate, ethylhexyl palmitate, isocetyl stearate, octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

In some embodiments, fatty esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- and/or pentahydroxy alcohols can be used in the oil phase. For example, the esters can include diethyl sebacate; diisopropyl sebacate; diisopropyladipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityltetrai sononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and/or polyethylene glycol di stearates.

In some embodiments, the fatty esters are selected from ethyl, isopropyl, myristyl, cetyl palmitate, stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; isocetyl stearate, dioctyl malate, hexyl laurate, 2-hexyldecyl laurate, isononyl isononanoate and cetyl octanoate. In some embodiments, the fatty esters are selected from cetyl palmitate, 2-ethylhexyl palmitate, isocetyl stearate, and any combination thereof. In some embodiments, the fatty esters are selected from cetyl palmitate, 2-ethylhexyl palmitate, and any combination thereof. In some embodiments, the fatty esters are selected from cetyl palmitate, isocetyl stearate, and any combination thereof. In some embodiments, the fatty ester is cetyl palmitate.

In some embodiments, the fatty esters can include sugar esters and diesters of $C_6$-$C_{30}$ fatty acids (e.g., $C_{12}$-$C_{22}$ fatty acids). As used herein, the term "sugar" refers to oxygen-bearing hydrocarbon-based compounds containing several alcohol functions, with or without aldehyde or ketone functions, and which contain at least 4 carbon atoms. These sugars may be monosaccharides, oligosaccharides or polysaccharides. Examples of suitable sugars include sucrose (or saccharose), glucose, galactose, ribose, fructose, maltose, mannose, arabinose, xylose and lactose, and derivatives thereof, alkyl derivatives thereof, such as methyl derivatives thereof, for instance methylglucose.

In some embodiments, the sugar esters of fatty acids are selected from the esters or mixtures of esters of sugars described previously and of linear or branched, saturated or unsaturated $C_6$-$C_{30}$ fatty acids (e.g., $C_{12}$-$C_{22}$ fatty acids). If the sugar esters of fatty acids are unsaturated, these compounds can include one to three conjugated or non-conjugated carbon-carbon double bonds. Esters according to this variant can include mono-, di-, tri-, tetraesters and polyesters, and mixtures thereof. These esters can be selected, for example, from oleates, laurates, palmitates, myristates, behenates, cocoates, stearates, linoleates, linolenates, caprates and arachidonates, or mixtures thereof such as oleo-palmitate, oleo-stearate and palmito-stearate mixed esters. In some embodiments, the sugar esters of fatty acids are monoesters and diesters, such as sucrose, glucose or methylglucose mono- or dioleates, stearates, behenates, oleopalmitates, linoleates, linolenates and oleo stearates.

In some embodiments, the fatty esters can include synthetic oils. As compared to the natural oils which have 3 chains of fatty acids (e.g., triglycerides), synthetic oils can have one fatty acid chain. Based on the variety of fatty acids and alcohols (e.g. butyl, isopropyl, ethylhexyl, myristyl, oleyl alcohol, cetyl), a wide range of synthetic oils can be obtained.

Other Fatty Materials

In some embodiments, in addition to the at least one linear fatty ester, the oil phase can further include any of a number of fatty materials (which can be an oil, an ester, or a wax; or components of an oil, an ester, or a wax), such as oils of animal or plant origin (described above), synthetic glycerides, esters of fatty alcohols and/or fatty acids (described above) other than animal or plant oils and synthetic glycerides, fatty alcohols, non-salified fatty acids, silicone oils and aliphatic hydrocarbons, and mixtures thereof. These fatty materials may be volatile or non-volatile. In some embodiments, the oil phase further includes a component selected from aliphatic hydrocarbons, plant oils, fatty alcohols, esters of fatty alcohols and/or fatty acids other than animal or plant oils and synthetic glycerides, and mixtures thereof. In certain embodiments, the oil phase further includes a component selected from aliphatic hydrocarbons.

Examples of aliphatic hydrocarbons include vaseline or petrolatum, naphthalenes, and the like; hydrogenated polyisobutene, isoeicosan, polydecenes, hydrogenated polyisobutenes such as Parleam, and decene/butene copolymer; and mixtures thereof. Examples of aliphatic hydrocarbons, can also include linear, branched, or cyclic $C_6$-$C_{16}$ lower alkanes. Examples of aliphatic hydrocarbons include hexane, undecane, dodecane, tridecane and isoparaffins such as isohexadecane and isodecane.

Examples of synthetic glycerides include caprylic/capric acid triglycerides, for instance those sold by the company Stearineries Dubois or those sold under the names Miglyol 810, 812 and 818 by the company Dynamit Nobel.

Examples of silicone oils include linear organopolysiloxanes such as dimethylpolysiloxane, methylphenylpolysiloxane, methylhydrogenpolysiloxane, and the like; cyclic organopolysiloxanes such as octamethylcyclotetrasiloxane, decamethylcyclopentasiloxane, dodecamethylcyclohexasiloxane, and the like; and mixtures thereof.

In some embodiments, the oil phase includes at least one fatty acid. The fatty acids can be in acidic form, can be saturated or unsaturated, can contain from 6 to 30 carbon atoms (e.g., from 9 to 30 carbon atoms), and can be optionally substituted (e.g., with one or more hydroxyl groups, such as 1 to 4 hydroxyl groups). The unsaturated fatty acids can include one to three conjugated or non-conjugated carbon-carbon double bonds. The fatty acid can include, for example, myristic acid, palmitic acid, stearic acid, behenic acid, oleic acid, linoleic acid, linolenic acid, and/or isostearic acid.

In some embodiments, the oil phase includes at least one fatty alcohol. As used herein, "fatty alcohol" refers to any saturated or unsaturated, linear or branched $C_8$-$C_{30}$ fatty alcohol, which can be optionally substituted (e.g., with one or more hydroxyl groups, such as 1 to 4 hydroxyl groups). In some embodiments, unsaturated fatty alcohols can include one to three conjugated or non-conjugated carbon-carbon double bonds. In some embodiments, the fatty alcohol is unsaturated and/or branched.

In some embodiments, the fatty alcohols are $C_{12}$-$C_{22}$ fatty alcohols. The fatty alcohols can include, for example, isostearyl alcohol, oleyl alcohol, linoleyl alcohol, undecylenyl alcohol, palmitoleyl alcohol, linolenyl alcohol, erucyl alcohol, and mixtures thereof. In some embodiments, cetyl alcohol, stearyl alcohol or a mixture thereof (e.g., cetearyl alcohol), as well as myristyl alcohol, can be used as a solid fatty material. In some embodiments, isostearyl alcohol can be used as a liquid fatty material. In one embodiment, the oil phase includes cetyl alcohol.

Non-Ionic Surfactants

As discussed above, the compositions of the present disclosure includes at least one non-ionic surfactant. In some embodiments, the at least one non-ionic surfactant is present in a given composition in an amount of up to 10% by weight of the undiluted non-ionic surfactant (e.g., up to 8% by weight), relative to the total weight of the composition. For example, the at least one non-ionic surfactant can be present in the composition in an amount of 1% or more (e.g., 2% or more, 3% or more, 4% or more, 5% or more, 7% or more, or 8% or more) and/or 10% or less (e.g., 8% or less, 7% or less, 5% or less, 4% or less, 3% or less, or 2% or less) by weight of the undiluted non-ionic surfactant, relative to the total weight of the composition. In some embodiments, the at least one non-ionic surfactant is present in the composition in an amount of from 4 to 8% by weight of the undiluted non-ionic surfactant, relative to the total weight of the composition.

The nonionic surfactant of the present disclosure can have a hydrophilic-lipophilic balance (HLB) value of 18.0 or less (e.g., from 4.0 to 18.0, from 6.0 to 15.0, from 9.0 to 13.0, or from 9.0 to 11.0). For example, the nonionic surfactant of the present disclosure can have a hydrophilic-lipophilic balance (HLB) value of 18.0 or less (e.g., 15.0 or less, 13.0 or less, 10.0 or less, 5.0 or less, or 3.0 or less). In some embodiments, the nonionic surfactant is selected from esters of polyols with fatty acids with a saturated or unsaturated chain containing for example from 8 to 24 carbon atoms (e.g., 12 to 22 carbon atoms), and alkoxylated derivatives thereof, such as glyceryl esters of a $C_8$-$C_{24}$ fatty acid or acids and alkoxylated derivatives thereof, polyethylene glycol esters of a $C_8$-$C_{24}$ fatty acid or acids and alkoxylated derivatives thereof, sorbitol esters of a $C_8$-$C_{24}$ fatty acid or acids and alkoxylated derivatives thereof, sugar (sucrose, glucose, alkylglycose) esters of a $C_8$-$C_{24}$ fatty acid or acids and alkoxylated derivatives thereof, ethers of fatty alcohols, ethers of sugar and a $C_8$-$C_{24}$ fatty alcohol or alcohols, and mixtures thereof.

In some embodiments, the non-ionic surfactant is selected from PEG-20 glyceryl triisostearate, PEG-7 glyceryl cocoate, PEG-20 methylglucoside sesquistearate, PG-5 dioleate, PG-4 diisostearate, PG-10 isostearate, PEG-8 stearate, PEG-8 isostearate, PEG-60 hydrogenated castor oil, and any combination thereof. In some embodiments, the non-ionic surfactant is PEG-20 glyceryl triisostearate.

Fillers

In some embodiments, the compositions of the present disclosure further include at least one filler. In some embodiments, the at least one filler is present in a given composition in an amount of up to 20% by weight (e.g., up to 15% by weight, up to 10% by weight, up to 5% by weight, or up to 1% by weight), relative to the total weight of the composition. For example, the at least one filler can be present in the composition in an amount of 0.1% or more (e.g., 0.5% or more, 1% or more, 5% or more, 10% or more, or 15% or more) and/or 20% or less (e.g., 15% or less, 10% or less, 5% or less, 1% or less, or 0.5% or less) by weight, relative to the total weight of the composition. In some embodiments, the at least one filler is present in a given composition in an amount of from 0.1% to 10% (e.g., 0.1% to 1%, or 0.5%) by weight, relative to the total weight of the composition.

Examples of fillers include silica silylate, kaolin, lauryl lysine, talc, bentone, cellulose beads (i.e., cellulobeads USF, available for example from Daito Kasei Kogyo), and any combination thereof. In some embodiments, the compositions include 0.1% to 1% (e.g., 0.5%) by weight of silica silylate, relative to the total weight of the composition. In certain embodiments, the compositions include 0.1% to 1% (e.g., 0.5%) by weight of silica silylate and 0.1% to 1% (e.g., 0.5%) by weight of cellulose beads, relative to the total weight of the composition.

The fillers (e.g., cellulose beads) can provide beneficial effects such as oil control, sebum control, sweat control, mattefying effects, and/or skin protective effects such as the ability to absorb pollutant particles to a composition.

Other Components

The compositions of the present disclosure can further include other components, such as phenylethyl resorcinol (i.e., Symwhite377, Symrise), capryloyl salicylic acid (i.e., LHA, Chimex), and a combination thereof. In some embodiments, the compositions of the present disclosure can include fragrances, antioxidants (e.g., vitamin E), plant extracts, and/or colorants.

In some embodiments, components such as fragrances, antioxidants, plant extracts, colorants, phenylethyl resorcinol, and capryloyl salicylic acid can each be present in a given composition in an amount of up to 5% by weight (e.g., up to 4% by weight, up to 3% by weight, up to 2% by weight, up to 1% by weight, or up to 0.5% by weight), relative to the total weight of the composition. For example, components such as fragrances, antioxidants, plant extracts, colorants, phenylethyl resorcinol, and capryloyl salicylic acid can each be present in a given composition in an amount of 0.01% or more (e.g., 0.05% or more, 0.1% or more, 0.5% or more, 1% or more, 1.5% or more, 2% or more, 3% or more, or 4% or more) and/or 5% or less (e.g., 4% or less, 3% or less, 2% or less, 1.5% or less, 1% or less, 0.5% or less, 0.1% or less, or 0.05% or less) by weight, relative to the total weight of the composition.

Formulations

In some embodiments, the composition includes 5-10% by weight isocetyl stearate, 45-55% by weight of ethylhexyl palmitate, 0.5% by weight of silica silylate, 15-25% by weight of cetyl palmitate, 5-7% by weight of polyethylene, 1% by weight of olive oil, 1-2% by weight of shea butter, 2% by weight of cetyl alcohol, 0.1-2% by weight of caprylyl glycol, 5% by weight of PEG-20 glyceryl triisostearate, 5% by weight of neopentyl glycol diheptanoate, 0.5% by weight of tocopherol, and 0.1-1% by weight of plant extract and fragrance.

It is understood that for the compositions of the present disclosure, the sum of the percentages of the various components in any given composition is 100%, even though the sum of the ranges of the composition components may exceed 100%.

Properties of the Compositions

Figure 1:
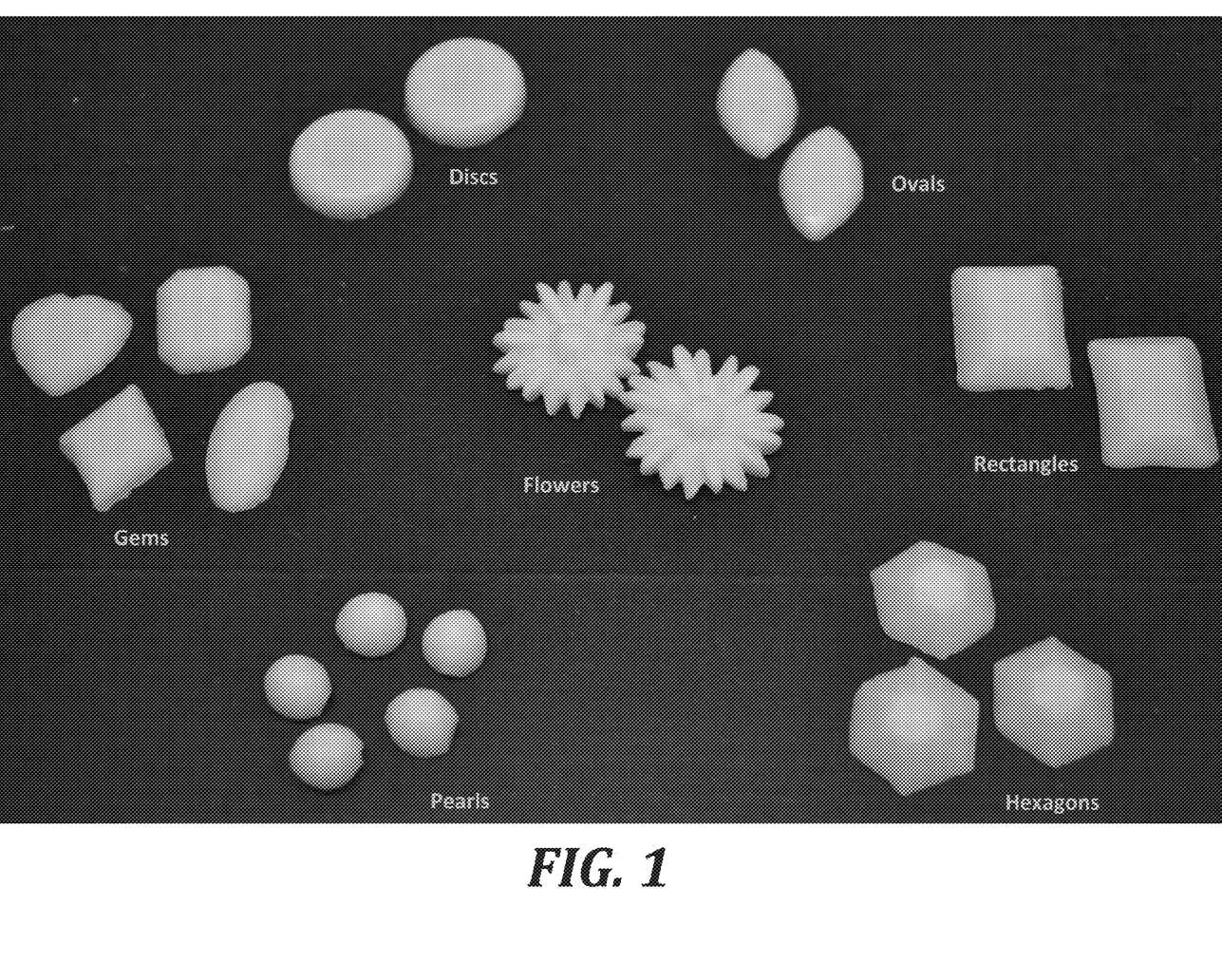
FIG. 1 is a photograph of exemplary solid molded compositions in accordance with embodiments disclosed herein.

The compositions of the present disclosure can have a number of desirable properties. For example, the compositions can be molded via hot-pouring techniques. Examples of molded compositions disclosed herein are shown in FIG. 1. The compositions can retain a molded shape when subjected to a pop-out test (described below in Example 2) at ambient temperature. As used herein, "ambient temperature" refers to a temperature of from 20 to 30° C. As used herein, the term "about" indicates that the subject number can be increased or decreased by 5% and still fall within the embodiment described or claimed.

In some embodiments, the compositions can be solid at ambient temperature with a hardness of at least 35 g-force (e.g., at least 60 g-force). In some embodiments, the compositions have a hardness of 35 g-force or more (e.g., 40 g-force or more, 60 g-force or more, 80 g-force or more, or 100 g-force or more) and/or 130 g-force or less (e.g., 100 g-force or less, 80 g-force or less, 60 g-force or less, or 45 g-force or less), when the hardness is measured at ambient temperature. In certain embodiments, the compositions have a hardness of from 35 g-force to 130 g-force (e.g., from 60 g-force to 110 g-force), when the hardness is measured at ambient temperature. The hardness can be measured using a texture analyzer, using a procedure as described below in Example 1. In some embodiments, the hardness is measured after (e.g., 12 or more hours, or 12-24 hours after) forming a molded composition (e.g., via hot-pouring techniques) and can range from 60 g-force to 130 g-force, when measured at ambient temperature. In certain embodiments, the hardness is measured after performing a series of stability measurements at a variety of temperatures (e.g., 5° C., 10° C., 25° C., and 45° C.) on the molded composition; where the hardness can range from 35 g-force to 130 g-force, when measured at ambient temperature. As used herein, "ambient temperature" refers to a temperature of from 20 to 30° C.

In some embodiments, the compositions of the present disclosure can be used to remove makeup and/or dirt and can provide excellent cleansing ability. When cleansing with the compositions, the compositions can be used alone, manually, or with an implement or electronic device on wet or dry skin. In some embodiments, the compositions can be removed through emulsification with water or by wiping the compositions from the skin with a dry or wet substrate. When applied either manually or using an electronic device to a skin portion, the compositions can undergo a solid to cream (e.g., a creamy oil) transition over a period spanning from an initial application up to, but not limited to 5 minutes, at ambient temperature. As used herein, "cream" refers to a composition having a high viscosity that is softer than the solid and that is spreadable at ambient temperature.

Methods of Use

In use, a user can apply a given composition of the present disclosure at ambient temperature (i.e., a temperature of from 20 to 30° C.). The composition can be applied to a skin portion to cleanse the skin portion (e.g., to remove makeup and/or dirt from the skin portion).

In some embodiments, the composition is applied manually. For example, the composition can be applied using fingertips onto a composition on a skin portion. As another example, the composition can be applied by manually wiping or massaging a composition on a skin portion using an applicator, a sponge, a towel, or a tissue.

In certain embodiments, the force is applied by an electronic device.

The following examples are included for the purpose of illustrating, not limiting, the disclosed embodiments. Example 1 describes procedures for analyzing a texture of a composition. Example 2 describes procedures for performing a pop-out test. Example 3 describes procedures for evaluating texture transformations and skin feel of embodiments of the comparative compositions and compositions of the present disclosure. Example 4 presents some exemplary compositions and comparative compositions.

EXAMPLES

Example 1. Texture Analysis Methods

The texture analysis results and characteristics described above are in the context of the following method.

A texture analyzer of the following make and settings was used.

Make: Stable Micro Systems Texture Analyser
Model: TA-XT Plus
Test Method:
Test Mode: Compression
Pre-Test speed: 0.50 mm/sec
Test Speed: 1.00 mm/sec
Post Test Speed: 10.00 mm/sec
Distance: 5.0 mm
Trigger force: 0.049N, or 5 g
Probe: P/2 (TA-52) 2 mm diameter cylinder stainless steel, 3.144 mm$^2$ contact area
Hardness/firmness=the peak or maximum force (in grams) of a $1^{st}$ compression of a probe into a sample.

Sample preparation method: Samples were prepared by hot-pouring the batch into 1 oz glass jars that were allowed to cool and equilibrate overnight (i.e., 12-24 hours) before taking the initial reading at ambient temperature. Each sample was measured 3 times and the average hardness/firmness of the sample was calculated through averaging the 3 highest peaks from the 3 measurements. The probe was raised and cleaned through wiping with a Kim wipe after each measurement.

Example 2. Moldability "Pop-Out" Test Methods

Moldability Test: Pass or Fail

Once all ingredients are incorporated into the batch at high temperatures, the composition was then poured (while still fluid/hot) into molds. The samples were covered lightly with a kimwipe to ensure no dust or contaminates settle into the samples. After 24 hours, the molds were turned over and pushed lightly to "pop-out" the samples. A sample passes this test if the composition pops-out cleanly and evenly from the mold. A sample fails this test if >10% of the sample remains in the mold, if the sample breaks, crumbles and does not pop-out of the mold evenly.

Example 3. Texture Transformation and Skin Feel Test Methods

Texture transformation/skin feel test: 1-3 scale, 1=good; 2=moderate; 3=poor

Once a sample passed the Moldability test, it was then assessed in a texture transformation/skin feel test. The sample was spread/rubbed manually onto the skin for a period of up to 1 minute and assessed at ambient temperature for several attributes: dragginess/spreadability, even deposition/crumbling, creaminess, lubricity/plastic feel, good/poor rinse ability. A 1 (best) or 2 rating was acceptable, whereas a 3 (poor) rating eliminated this composition since these attributes are necessary for consumer acceptance. Results are shown in FIGS. 2-4.

Example 4. Exemplary Compositions and Comparative Compositions

Figure 4:
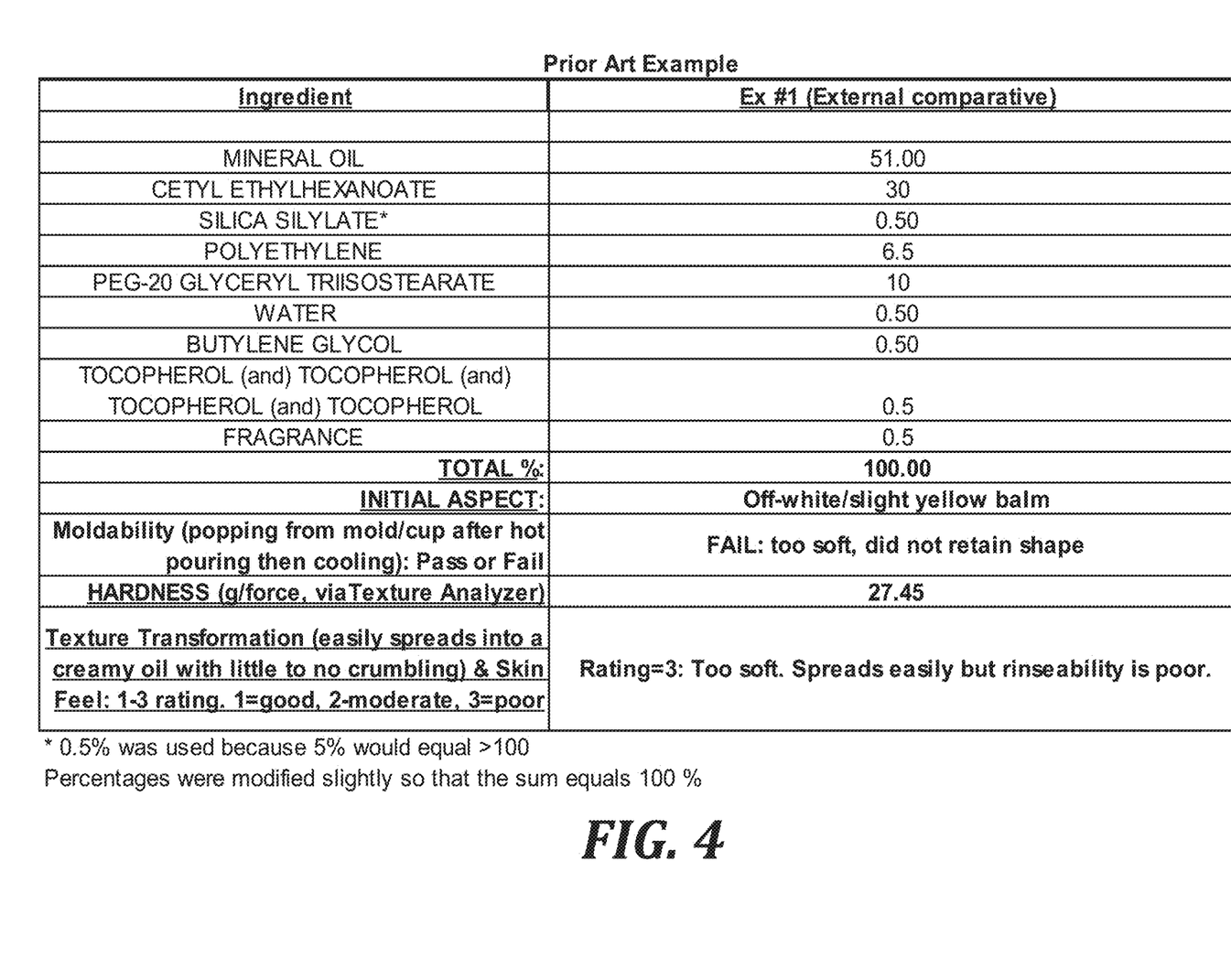
FIG. 4 is a table providing compositional and testing information regarding a comparative composition according to the prior art.

FIGS. 2-4 are tables that provide both compositional information, as well as texting results for comparative samples (FIG. 2), exemplary compositions (FIG. 3), and a formulation identified in KR101347727 (FIG. 4) that was recreated as closely as possible.

Tests were performed, including moldability, hardness, and texture transformation. Results are shown in FIGS. 2-4.

Figure 5:
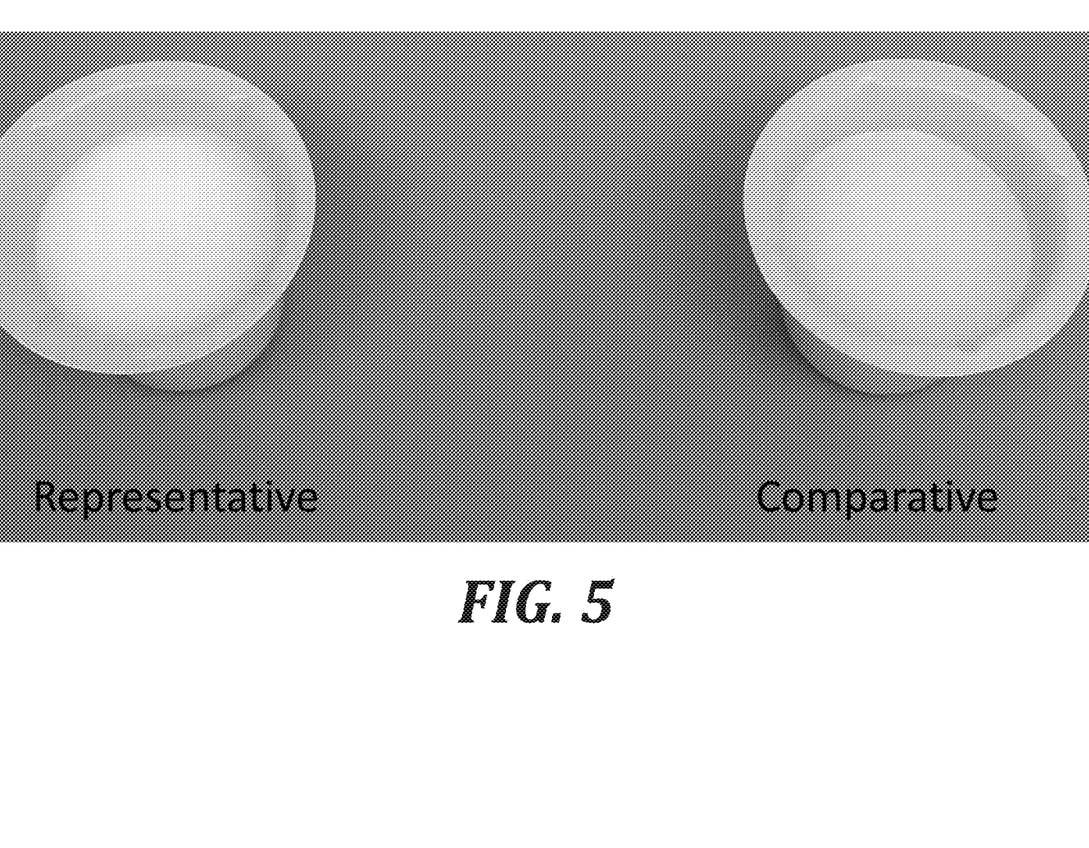
FIGS. 5-8 are photographs of side-by-side comparisons between an exemplary composition and a prior art composition subjected to the various stages of the "pop-out" test, as disclosed herein.
Figure 6:
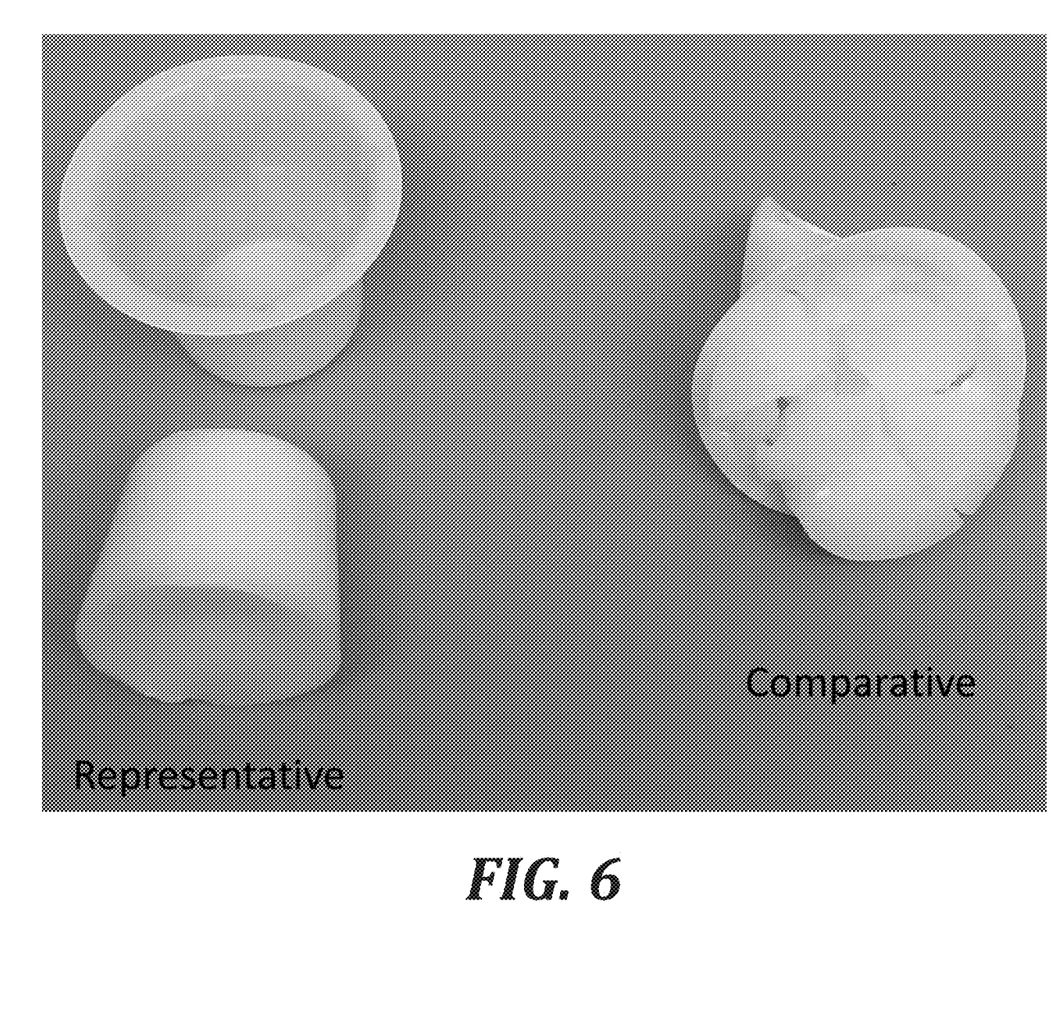
Figure 7:
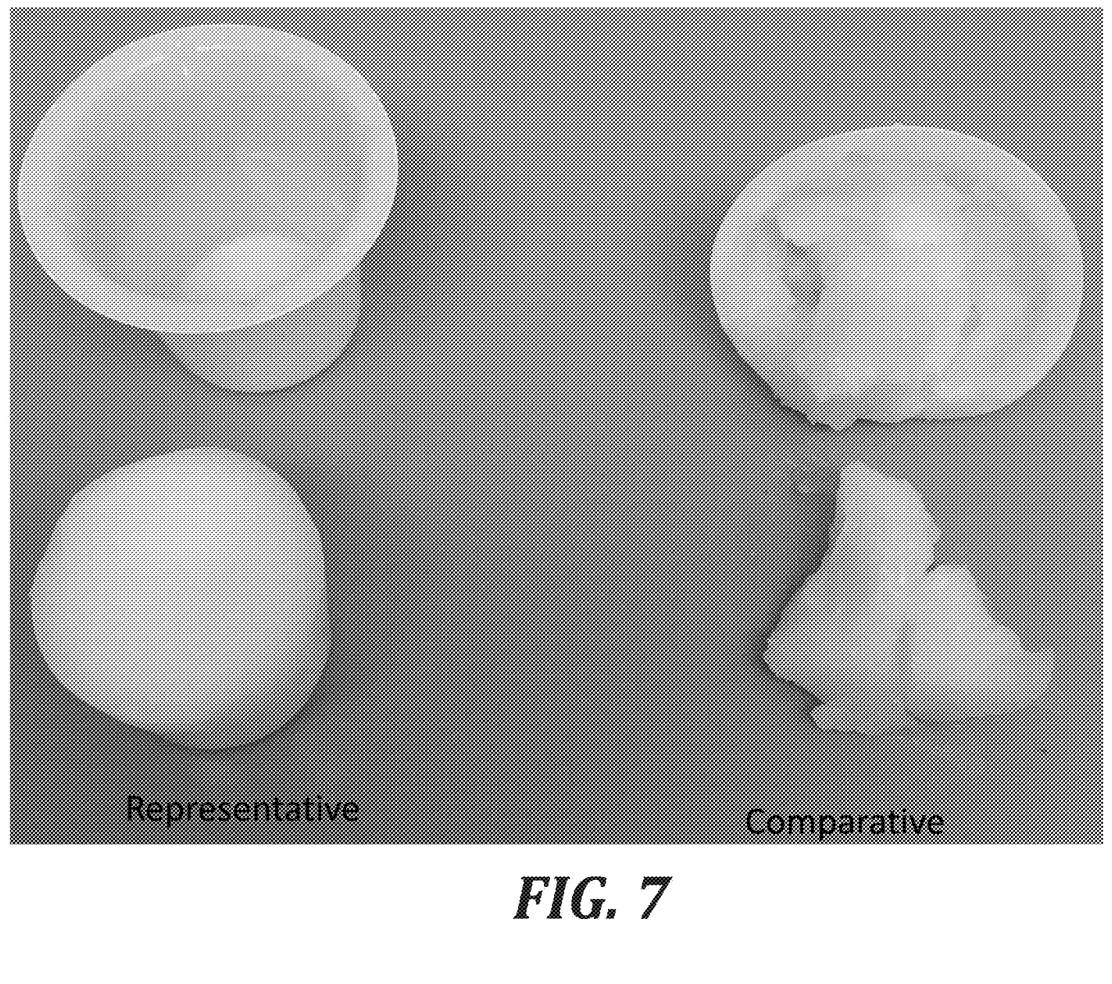
Figure 8:
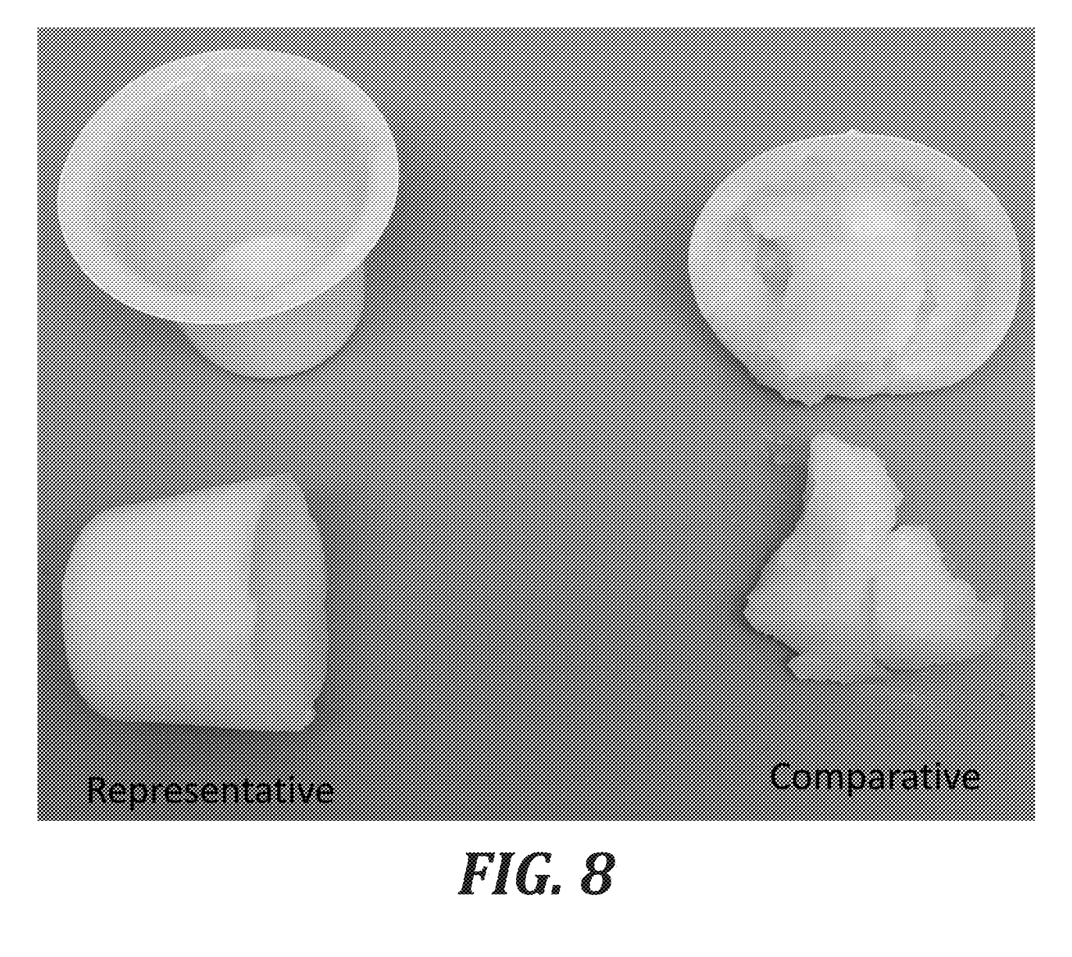

FIGS. 5-8 show a representative composition corresponding to Ex. #13 in FIG. 3 of the present disclosure (left hand sample) and a comparative composition corresponding to the composition in FIG. 4 (right hand sample). FIG. 5 is a photograph showing a representative composition corresponding to Ex. #13 in FIG. 3 of the present disclosure (left hand sample) and a comparative composition corresponding to the composition in FIG. 4 (right hand sample) prior to the pop-out test. As shown in FIGS. 6-8, the representative composition corresponding to Ex. #13 in FIG. 3 of the present disclosure (left hand sample in each of FIGS. 5-8) satisfy the pop-out test and pops out wholly, cleanly, and evenly from the mold; while the comparative composition corresponding to the composition in FIG. 4 cannot pop out cleanly and evenly from the mold, crumbling instead during the test.

Therefore, the moldable cosmetic compositions passed the stability criteria over time and at different temperatures, passed a pop-out test confirming moldability, could transition from a solid to a creamy oil in an aesthetically pleasing manner and provided a cleansing benefit. The linear/unbranched fatty esters enabled a moldable composition without a trade-off in the composition aesthetics and skin benefits (vs. a higher level of high melting point waxes only).

While illustrative embodiments have been illustrated and described, it will be appreciated that various changes can be made therein without departing from the spirit and scope of the invention.

The embodiments of the invention in which an exclusive property or privilege is claimed are defined as follows:

1. An anhydrous composition, consisting of:
   (a) an oil phase consisting of one or more linear fatty esters and optionally an agent selected from ethylhexyl palmitate, isocetyl stearate, olive oil, shea butter, linseed oil, camellia oil, macadamia nut oil, sunflower oil, apricot oil, soybean oil, arara oil, hazelnut oil, corn oil, avocado oil, sasanqua oil, castor oil, safflower oil, jojoba oil, sunflower oil, almond oil, grapeseed oil, sesame oil, soybean oil, peanut oil, avocado butter, cocoa butter, squalene, perhydrosqualene, a polyethylene wax, a synthetic wax, a carnauba wax, a microcrystalline wax, an ozokerite, a hydrogenated jojoba oil, and any combination thereof;
   (b) one or more non-ionic surfactants;
   (c) an optional filler selected from silica silylate, kaolin, lauryl lysine, talc, bentone, cellulose beads, and any combination thereof; and
   (d) optionally phenylethyl resorcinol, caprylolyl salicylic acid, or a combination thereof,
   wherein the anhydrous composition:
   has less than 1% by weight water;
   is solid at ambient temperature with a hardness of at least 35 g-force;
   retains a molded shape when subjected to a pop-out test at ambient temperature;
   undergoes a solid to cream transition over a period spanning from an initial application up to 1 to 5 minutes at ambient temperature, when applied manually or using an electronic device to a skin portion; and
   does not comprise paraffin wax, mineral oil, an anionic surfactant, or any combination thereof.

2. The anhydrous composition of claim 1, wherein the composition has a hardness of 35 to 130 g-force when the hardness is measured at ambient temperature.

3. The anhydrous composition of claim 1, wherein the one or more linear fatty esters are present in an amount of 1% to 30% by weight.

4. The anhydrous composition of claim 1, wherein the linear fatty ester is cetyl palmitate.

5. The anhydrous composition of claim 1, wherein the ethylhexyl palmitate, isocetyl stearate, or any combination thereof is present in an amount of 1% to 60% by weight.

6. The anhydrous composition of claim 1, wherein the olive oil, shea butter, linseed oil, camellia oil, macadamia nut oil, sunflower oil, apricot oil, soybean oil, arara oil, hazelnut oil, corn oil, avocado oil, sasanqua oil, castor oil, safflower oil, jojoba oil, sunflower oil, almond oil, grapeseed oil, sesame oil, soybean oil, peanut oil, avocado butter, cocoa butter, squalene, perhydrosqualene, or any combination thereof is present in an amount of 1% to 20% by weight.

7. The anhydrous composition of claim 1, wherein the polyethylene wax, synthetic wax, carnauba wax, microcrystalline wax, ozokerite, hydrogenated jojoba oil, or any combination thereof is present in an amount of 1% to 15% by weight.

8. The anhydrous composition of claim 1, wherein the one or more non-ionic surfactants are present in an amount of up to 10% by weight of an undiluted non-ionic surfactant.

9. The anhydrous composition of claim 1, wherein the one or more non-ionic surfactants have an HLB of 18.0 or less.

10. The anhydrous composition of claim 9, wherein the one or more non-ionic surfactants are selected from the group consisting of PEG-20 glyceryl triisostearate, PEG-7 glyceryl cocoate, PEG-20 methylglucoside sesquistearate, PG-5 dioleate, PG-4 diisostearate, PG-10 isostearate, PEG-8 stearate, PEG-8 isostearate, PEG-60 hydrogenated castor oil, and any combination thereof.

11. The anhydrous composition of claim 1, wherein the composition consists of 70% to 95% by weight of the oil phase, of which 1% to 30% by weight of the oil phase is the one or more linear fatty esters; 4% to 8% by weight of the one or more non-ionic surfactants; and a balance consisting of the filler, phenylethyl resorcinol, caprylolyl salicylic acid, or any combination thereof.

12. A method of cleansing, comprising applying a composition of claim 1 at ambient temperature.

13. The method of claim 12, wherein the anhydrous composition of claim 1 is delivered to a skin portion to cleanse the skin portion.

14. The method of claim 13, wherein cleansing the skin portion comprises removing makeup or dirt from the skin portion.

15. The method of claim 12, wherein the composition is applied manually.

16. The method of claim 12, wherein the composition is applied by an electronic device.

* * * * *